(12) United States Patent
Jabbari

(10) Patent No.: US 10,836,994 B2
(45) Date of Patent: *Nov. 17, 2020

(54) KERATIN ALLYL THIOETHER THREE-DIMENSIONAL CELL CULTURE SYSTEM

(71) Applicant: University of South Carolina, Columbia, SC (US)

(72) Inventor: Esmaiel Jabbari, Bethesda, MD (US)

(73) Assignee: University of South Carolina, Columbia, SC (US)

(*) Notice: Subject to any disclaimer, the term of this patent is extended or adjusted under 35 U.S.C. 154(b) by 246 days.

This patent is subject to a terminal disclaimer.

(21) Appl. No.: 15/814,584

(22) Filed: Nov. 16, 2017

(65) Prior Publication Data

US 2018/0273899 A1 Sep. 27, 2018

Related U.S. Application Data

(60) Provisional application No. 62/474,677, filed on Mar. 22, 2017.

(51) Int. Cl.
*C12N 5/00* (2006.01)
*C07K 14/47* (2006.01)
*C12N 9/76* (2006.01)

(52) U.S. Cl.
CPC ........ *C12N 5/0018* (2013.01); *C07K 14/4741* (2013.01); *C12N 5/0068* (2013.01); *C12N 9/6427* (2013.01); *C12Y 304/21004* (2013.01); *C12Y 304/24* (2013.01); *C12N 2533/50* (2013.01); *C12N 2537/10* (2013.01)

(58) Field of Classification Search
CPC .............. C12N 5/0068; C12N 2533/50; C12N 2537/10; C12N 9/6427; C12N 5/0018; C12Y 304/24; C12Y 304/21004; C07K 14/4741

See application file for complete search history.

(56) References Cited

PUBLICATIONS

Barati D. et al., "Synthesis and Characterization of Photo-Cross-Linkable Keratin Hydrogels for Stem Cell Encapsulation", Biomacromolecules, published in print 2017 (online published on Dec. 21, 2016), vol. 18, pp. 398-412. (Year: 2017).*
Wang S. et al., "Culturing fibroblasts in 3D human hair keratin hydrogels", Applied Materials and Interfaces, 2015, vol. 7, pp. 5187-5198. (Year: 2015).*
Annabi et al., 25th Anniversary Article: Rational Design and Applications of Hydrogels in Regenerative Medicine, Advanced Materials, 26, 2014, 85-124.
Aoyama, et al., Keratin Nanofiber Scaffold for Vascular Graft (Abstract Only), Tissue Engineering Part A, 21, 2015, S244.
Arai et al., Amino acid sequence of feather keratin from fowl, European Journal of Biochemistry, 132, 1983, 506-507.
Balaji et al., Characterization of keratincollagen 3D scaffold for biomedical applications, Polymers for Advanced Technologies, 23, 2012, 500-507.
Barati et al., Effect of Organic Acids on Calcium Phosphate Nucleation and Osteogenic Differentiation of Human Mesenchymal Stem Cells on Peptide Functionalized Nanofibers, Langmuir, 31, 2015, 5130-5140.
Barati et al., Spatiotemporal release of BMP-2 and VEGF enhances osteogenic and vasculogenic differentiation of human mesenchymal stem cells and endothelial colony-forming cells coencapsulated in a patterned hydrogel, Journal of Controlled Release, 223, 2016, 126-136.
Barati et al., Time dependence of material properties of polyethylene glycol hydrogels chain extended with short hydroxy acid segments, Polymer, 55, 2014, 3894-3904.
Barone et al., Thermally processed keratin films, Journal of Applied Polymer Science, 97, 2005, 1644-1651.
Bernardes et al., Facile conversion of cysteine and alkyl cysteines to dehydroalanine on protein surfaces: versatile and switchable access to functionalized proteins, Journal of the American Chemical Society, 2008;130:5052-3.
Bhardwaj et al., Silk fibroin-keratin based 3D scaffolds as a dermal substitute for skin tissue engineering, Integrative Biology, 7, 2015, 53-63.
Burnett et al., Hemostatic properties and the role of cell receptor recognition in human hair keratin protein hydrogels, Biomaterials, 34, 2013, 2632-2640.
Chalker et al., Chemical modification of proteins at cysteine: opportunities in chemistry and biology, Chemistry—An Asian Journal, 4, 2009, 630-640.
Chan et al., Crosslinking of collagen scaffolds promotes blood and lymphatic vascular stability, Journal of Biomedical Materials Research Part A. 102, 2014, 3186-3195.
Chen et al., A Universal and Facile Approach for the Formation of a Protein Hydrogel for 3D Cell Encapsulation, Advanced Functional Materials, 25, 2015, 6189-98.
Chen et al., Engineering Vascularized Tissue Constructs using an Injectable Cell-laden Collagen Hydrogel (Abstract Only), Tissue Engineering Part A, 21, 2015, S102.

(Continued)

Primary Examiner — Satyendra K Singh
(74) Attorney, Agent, or Firm — Dority & Manning, P.A.

(57) ABSTRACT

A three-dimensional cell culture system that includes a keratin-based hydrogel precursor solution and a cell culture vessel is provided. The precursor solution includes solubilized keratin that has been functionalized to include a crosslinking moiety. The crosslinking moiety exhibits controllable crosslinking, e.g., a photopolymerizable crosslinking moiety. The crosslinking functionality is bonded to the keratin via cysteines following reduction of disulfide bonds of the native keratin. The precursor solution can be combined with cells to form a cell suspension that is disposed on a surface of the cell culture vessel. Alternatively, the cells can be added to a surface of a keratin-based hydrogel that has been formed on a surface of the cell culture vessel. The resulting three-dimensional cell culture system is a biomimetic/biologic, trypsin-degradable cell culture system for expansion of mammalian cells. The expanded cells are expected to possess a morphology similar to the primary cells prior to cultivation.

18 Claims, 7 Drawing Sheets

(56) References Cited

PUBLICATIONS

Dawson et al., Biomaterials for stem cell differentiation, Advanced drug delivery reviews, 60, 2008, 215-28.
Dong et al., In Situ "Clickable" Zwitterionic Starch-Based Hydrogel for 3D Cell Encapsulation, ACS Applied Materials & Interfaces, 8, 2016. 4442-55.
Dong et al., Injectable Hybrid Hydrogel for Mesenchymal Stem Cell Delivery, from PEG-based Multifunctional Hyperbranched Polymers (Abstract Only), Tissue Engineering Part A, 21, 2015, S298-S289.
Eastoe, The amino acid composition of mammalian collagen and gelatin, Biochemical Journal, 61, 1955, 589.
Ferlin et al., Development of a Dynamic Stem Cell Culture Platform for Mesenchymal Stem Cell Adhesion and Evaluation, Molecular Pharmaceutics, 11, 2014, 2172-2181.
Fraser et al., Keratins: their composition, structure, and biosynthesis: Charles C. Thomas, 1972.
Fuhrmann et al., Injectable hydrogel promotes early survival of induced pluripotent stem cell-derived oligodendrocytes and attenuates longterm teratoma formation in a spinal cord injury model, Biomaterials, 83, 2016, 23-36.
Golub et al., The Role of Alkaline Phosphatase in Cartilage Mineralization, Bone and Mineral, 17, 1992, 273-278.
Gorman, Materials Take Wing: What to do with 4 billion pounds of feathers?, Science News, 161, 2002, 120.
Guo et al., In vitro generation of an osteochondral construct using injectable hydrogel composites encapsulating rabbit marrow mesenchymal stem cells, Biomaterials, 30, 2009, 2741-2752.
Han et al., Alkylation of human hair keratin for tunable hydrogel erosion and drug delivery in tissue engineering applications, Acta Biomaterialia, 23, 2015, 201-213.
Haralson et al., Extracellular matrix. A practical approach, Annales de Biologie Clinique, 1996, 383-384.
He et al., Effect of grafting RGD and BMP-2 protein-derived peptides to a hydrogel substrate on osteogenic differentiation of marrow stromal cells, Langmuir, 24, 2008, 12508-12516.
Hoffman, Hydrogels for biomedical applications, Advanced drug delivery reviews, 64, 2012, 18-23.
Jayathilakan et al., Utilization of byproducts and waste materials from meat, poultry and fish processing industries: a review, Journal of Food Science and Technology, 49, 2012, 278-293.
Kakkar et al., Extraction and characterization of keratin from bovine hoof: A potential material for biomedical applications, Springerplus, 3, 2015, 596.
Karaman et al., Effect of surface modification of nanofibres with glutamic acid peptide on calcium phosphate nucleation and osteogenic differentiation of marrow stromal cells, Journal of Tissue Engineering and Regenerative Medicine, 10, 2016, E132-E146.
Karimi et al., A developmentally inspired combined mechanical and biochemical signaling approach on zonal lineage commitment of mesenchymal stem cells in articular cartilage regeneration, Integrative Biology, 7, 2015, 112-127.
Kelly et al., How to study proteins by circular dichroism, Biochimica et Biophysica Acta (BBA)—Proteins and Proteomics, 1751, 2005, 119-139.
Kwon et al., In vivo osteogenic differentiation of human turbinate mesenchymal stem cells in an injectable in situ-forming hydrogel, Biomaterials, 35, 2014, 5337-5346.
Lin et al., Allyl sulfides are privileged substrates in aqueous cross-metathesis: application to site-selective protein modification, Journal of the American Chemical Society, 130, 2008, 9642-9643.
Long et al., Improving the mechanical properties of collagen-based membranes using silk fibroin for corneal tissue engineering, Journal of Biomedical Materials Research Part A 103, 2015,1159-1168.
Lv et al., Structural and functional evaluation of oxygenating keratin/silk fibroin scaffold and initial assessment of their potential for urethral tissue engineering, Biomaterials, 84, 2016, 99-110.
Ma et al., Enhanced biological stability of collagen porous scaffolds by using amino acids as novel cross-linking bridges, Biomaterials, 25, 2004, 2997-3004.
Mabry et al., Microarray analyses to quantify advantages of 2D and 3D hydrogel culture systems in maintaining the native valvular interstitial cell phenotype, Biomaterials, 74, 2016, 31-41.
Moeinzadeh et al., B13Nanostructure Formation and Transition from Surface to Bulk Degradation in Polyethylene Glycol Gels Chain-Extended with Short Hydroxy Acid Segments, Biomacromolecules, 14, 2013, 2917-2928.
Moeinzadeh et al., Gelation Characteristics and Osteogenic Differentiation of Stromal Cells in Inert Hydrolytically Degradable Micellar Polyethylene Glycol Hydrogels, Biomacromolecules, 13, 2012, 2073-2086.
Munoz-Pinto et al., Collagen-mimetic hydrogels promote human endothelial cell adhesion, migration and phenotypic maturation. Journal of Materials Chemistry B. 3, 2015, 7912-7919.
Nichol et al., Cell-laden microengineered gelatin methacrylate hydrogels, Biomaterials, 31, 2010, 5536-5544.
Pace et al., A Human Hair Keratin Hydrogel Scaffold Enhances Median Nerve Regeneration in Nonhuman Primates: An Electrophysiological and Histological Study, Tissue Engineering Part A, 20, 2014, 507-517.
Patel et al., Biodegradable polymer scaffold for tissue engineering, Trends in Biomaterials and Artificial Organs, 25, 2011, 20-29.
Rehmann et al., Tuning microenvironment modulus and biochemical composition promotes human mesenchymal stem cell tenogenic differentiation, Journal of Biomedical Materials Research Part A, 104, 2016, 1162-1174.
Rouse et al., A Review of Keratin-Based Biomaterials for Biomedical Applications, Materials, 3, 2010, 999-1014.
Saravanan et al., Exploration on the Amino Acid Content and Morphological Structure in Chicken Feather Fiber, Journal of Textile and Apparel, Technology and Management, 7-3, 2012.
Sawada et al., Scaffold for Cell Culture Made by Electrospun Keratin Nanofibers (Abstract Only), Tissue Engineering Part A, 20, 2014, S65.
Stenman et al., Trypsin-2 degrades human type II collagen and is expressed and activated in mesenchymally transformed rheumatoid arthritis synovitis tissue, American Journal of Pathology, 167, 2005, 1119-1124.
Tan et al., Fabrication and Evaluation of Porous Keratin/chitosan (KCS) Scaffolds for Effectively Accelerating Wound Healing, Biomedical and Environmental Sciences, 28, 2015, 178-189.
Tanabe et al., Fabrication and characterization of chemically cross-linked keratin films, Materials Science and Engineering: C, 24, 2004, 441-446.
Tropel et al., Isolation and characterization of mesenchymal stem cells from adult mouse bone marrow, Experimental Cell Research, 295, 2004, 395-406.
Verma et al,, Preparation of scaffolds from human hair proteins for tissue-engineering applications, Biomedical materials, 3-2, 2008, 025007.
Wang et al., Human keratin hydrogels support fibroblast attachment and proliferation in vitro, Cell and Tissue Research, 347, 2012, 795-802.
Xu et al., Water-Stable Three-Dimensional Ultrafine Fibrous Scaffolds from Keratin for Cartilage Tissue Engineering, Langmuir, 30, 2014, 8461-8470.
Yamauchi et al., Preparation of stable aqueous solution of keratins, and physiochemical and biodegradational properties of films, Journal of biomedical materials research, 31, 1996, 439-444.
Yin et al., Study on effective extraction of chicken feather keratins and their films for controlling drug release, Biomaterials Science, 1, 2013, 528-536.
Yue et al., Synthesis, properties, and biomedical applications of gelatin methacryloyl (GelMA) hydrogels, Biomaterials, 73, 2015, 254-271.

* cited by examiner

KERATIN ALLYL THIOETHER THREE-DIMENSIONAL CELL CULTURE SYSTEM

RELATED APPLICATIONS

The present application claims priority to U.S. Provisional Application Ser. No. 62/474,677, filed on Mar. 22, 2017, which is incorporated herein in its entirety by reference thereto.

BACKGROUND

Cultivation and expansion of mammalian cells, including human or animal cells, on two-dimensional polystyrene or glass culture plates is not a benign process. First, cells on a two-dimensional culture plate are in an environment completely different from that in the natural tissue, where cells reside within a three-dimensional matrix of a tissue. During the culturing of cells on a two-dimensional surface, the cells must be treated with enzymes to degrade and detach the cells from the extracellular matrix (ECM) and other cells on the two-dimensional surface. Next, the released cells are passaged by removing the cells from the cell culture vessel in which they were cultured, and the released cells are then seeded onto new two-dimensional cell culture vessels (plates, flasks, dishes, etc.) at a low density. Thereafter, the cells are allowed to adhere to the plate and are expanded. After the cells reach confluency on the two-dimensional surface of the cell culture vessel, the cells are passaged by using trypsin, which is an enzyme that can detach the cells from the surface of the cell culture vessel. After exposure to trypsin, the cells are released from the surface of the cell culture vessel and are temporarily suspended in the culture medium. The resulting cell suspension is centrifuged, the cell culture medium is removed, and fresh cell culture medium is added to the remaining pellet of cells. The cells are then diluted in an appropriate amount of cell culture medium based on the number of cell culture vessels in which the cells are to be plated, and the cells are then split and reseeded into new cell culture plates for further expansion.

The aforementioned process of seeding primary cells, harvested from tissues, on two-dimensional culture vessel in which part of the cells' surface is attached to a rigid substrate while the other part faces the cell culture medium introduces a shock to the cells. The shock experienced by the cells leads to persistent production and activation of reactive oxygen species (RAS), leading to an imbalance in DNA damage/repair and DNA damage. Further, the shape of cells seeded on two-dimensional cell culture vessels is very different from those in natural tissues. As the cell phenotype, differentiation, and fate are shape dependent, the passage of cells on two-dimensional culture plates can lead to changes in phenotype. Further, the imbalance in the ratio of cell culture medium to cells can lead to hyperoxia, which can contribute to phenotypic heterogeneity amongst the passaged cells. Furthermore, when primary cells harvested from a tissue are plated, non-adherent cells, soluble proteins, and survival factors are removed from the suspension, which eventually leads to significant changes in cell fate. Despite these disadvantages, the two-dimensional cell culture system is used extensively for cell expansion because other options are limited. In particular, three-dimensional cell culture systems like collagen gels can be used for cell delivery in biomedical applications, but they are not useful for in vitro culturing and passaging of primary cells.

However, collagen-based hydrogels suffer from batch-to-batch variability in composition, limited thermal and mechanical stability, and relatively fast and uncontrolled degradation by matrix metalloproteinase enzymes (MMPs) secreted by the cells. The uncontrolled degradation of collagen gels by MMPs excludes the use of collagen gels as a matrix for cell passaging.

On the other hand, keratin is a family of fibrous proteins found in nature as the major component of wool, hair, horn, nail, and hoof in mammals, reptiles, crocodiles, and bird feather. Keratin contains peptide sequences and secondary structures that interact with cell surface receptors to promote cell adhesion. Subcutaneous implantation studies in animals demonstrate that keratin is biocompatible and does not cause an inflammatory response. In vitro studies with various cell types have shown that keratin as a matrix supports cell growth.

Keratin is an abundant natural protein found in poultry feather, animal hair and horn, and human hair. Due to its high strength and biocompatibility, keratin-based membranes, sponges, and fiber meshes have been developed as scaffolds for tissue engineering applications. Keratin has a relatively high fraction of cysteine residues (generally about 7 mole % to about 20 mole % of the total amino acid content) compared to other proteins, and partial alkylation of sulfhydryl groups of the cysteine residues combined with freeze drying and crosslinking have been used to produce porous keratin hydrogel scaffolds for cell seeding in tissue engineering applications. However, it would be beneficial if keratin scaffolds could sustain cell passaging via trypsin so that cells could be seeded and cultured on a three-dimensional matrix to maintain their phenotype and natural characteristics.

Specifically, a three-dimensional culture system for cell passaging should be biocompatible and allow for repeated detachment/separation and encapsulation/attachment of the cells from/to the three-dimensional substrate with tunable properties.

There is a need to develop a three-dimensional cell culture system with tunable properties for cell cultivation/expansion that allows for repeated cell attachment and detachment to/from the three-dimensional substrate. There is also a need for a three-dimensional cell culture system and method utilizing natural protein-based hydrogels that include features of the natural ECM with predictable amino acid composition that can be formed with predetermined degradation control and porosity characteristics to promote cell growth.

SUMMARY

According to one embodiment, a three-dimensional cell culture system is provided. The three-dimensional cell culture system includes a cell culture vessel and a keratin-based hydrogel formed from a keratin-based hydrogel precursor solution. The keratin-based hydrogel precursor solution includes a solubilized keratin-based polymer comprising a reactive functionality bonded to the keratin-based polymer via cysteine residues of the polymer, wherein about 10% or less of the cysteine residues of the solubilized keratin-based polymer are bonded via disulfide bridges.

In one particular embodiment, the reactive functionality can include allyl functionality, acrylate functionality, diacrylate functionality, oligoacrylate functionality, methacrylate functionality, dimethacrylate functionality, oligomethacrylate functionality, or any combination thereof.

In another embodiment, the keratin-based polymer can include keratin allyl thioether.

In still another embodiment, the keratin-based hydrogel precursor solution can include a crosslink initiator, wherein the crosslink initiator comprises an ultraviolet crosslink initiator, a visible light initiator, a thermal initiator, or a chemical initiator.

In yet another embodiment, the keratin-based hydrogel can be formed on a surface of the cell culture vessel. Further, the surface can include polystyrene or glass.

In addition, the three-dimensional cell culture system can be configured such that a suspension of cells is combined with the keratin-based polymer precursor solution before the keratin-based hydrogel is formed on the surface of the cell culture vessel, wherein the living cells are encapsulated within the keratin-based hydrogel. Alternatively, the three-dimensional cell culture system can be configured such that a suspension of cells is disposed on a surface of the keratin-based hydrogel after the keratin-based hydrogel is formed on the surface of the cell culture vessel.

In one more embodiment, the keratin-based hydrogel can be susceptible to degradation by trypsin.

In an additional embodiment, the keratin-based hydrogel is not susceptible to degradation by collagenase.

According to another embodiment of the present invention, a method of forming a three-dimensional cell culture system that includes a cell culture vessel and a keratin-based hydrogel is provided. The method includes forming a keratin-based hydrogel precursor solution, the solution comprising a solubilized keratin-based polymer comprising a reactive functionality bonded to the keratin-based polymer via cysteine residues of the polymer, wherein about 10% or less of the cysteine residues of the solubilized keratin-based polymer are bonded via disulfide bridges; delivering the keratin-based hydrogel precursor solution to a surface of the cell culture vessel; and following delivery, crosslinking the keratin-based polymer at the surface via reaction of the reactive functionality to form the keratin-based hydrogel.

In one particular embodiment, the keratin-based polymer can be crosslinked via addition of energy to the keratin-based hydrogel precursor solution. Further, the energy can be in the form of ultraviolet radiation, visible light, or infrared radiation.

In another embodiment, the keratin-based polymer can be crosslinked via addition of a crosslinking agent to the surface to form the keratin-based hydrogel. Further, cells can be added to the cell culture vessel after the crosslinking agent is added to the surface to form the keratin-based hydrogel, wherein the cells are delivered to a surface of the keratin-based hydrogel. Alternatively, the cells can be combined with the keratin-based hydrogel precursor solution before delivering the keratin-based hydrogel precursor solution to the surface of the cell culture vessel.

According to one more embodiment of the present invention, a method of culturing cells in a three-dimensional cell culture system that includes a cell culture vessel and a keratin-based hydrogel is provided. The method includes combining a first keratin-based hydrogel precursor solution with the cells; delivering the first keratin-based hydrogel precursor solution containing the cells to a surface of the cell culture vessel to form a film; crosslinking the film to form the keratin-based hydrogel; and adding a layer of cell culture medium to the cell culture vessel.

In more embodiment, the method can further include introducing trypsin to the cell culture vessel to detach the cells from the keratin-based hydrogel.

In an additional embodiment, the method can further include separating the detached cells from the trypsin and combining a second keratin-based hydrogel precursor solution with the detached cells.

In yet another embodiment, the method can include delivering the second keratin-based hydrogel precursor solution containing the detached cells to a surface of one or more new cell culture vessels.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
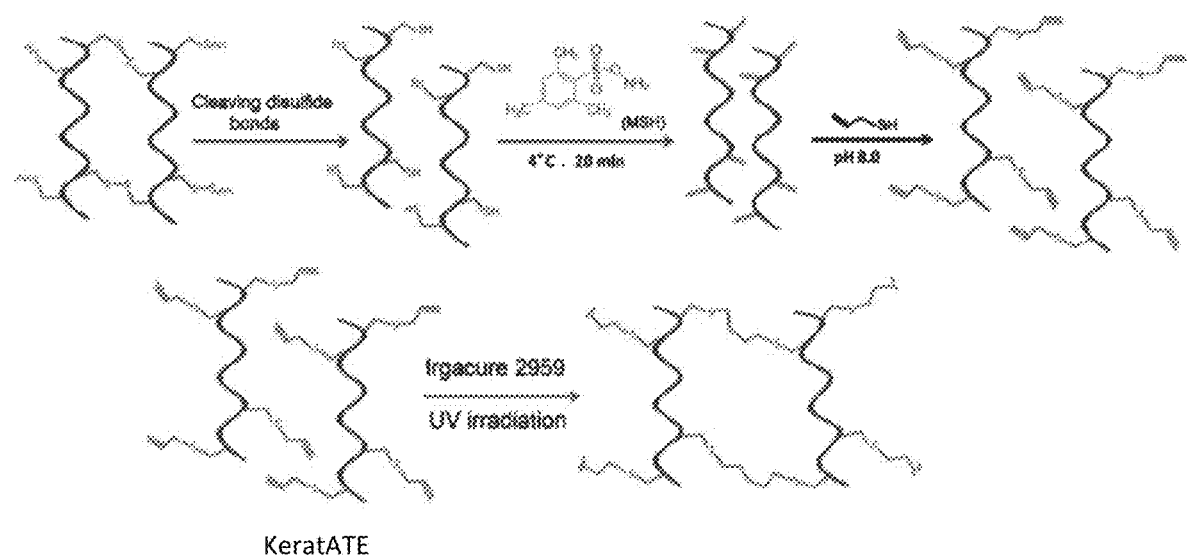
FIG. 1 illustrates a synthesis route for keratin allyl thioether.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

Figure 13:
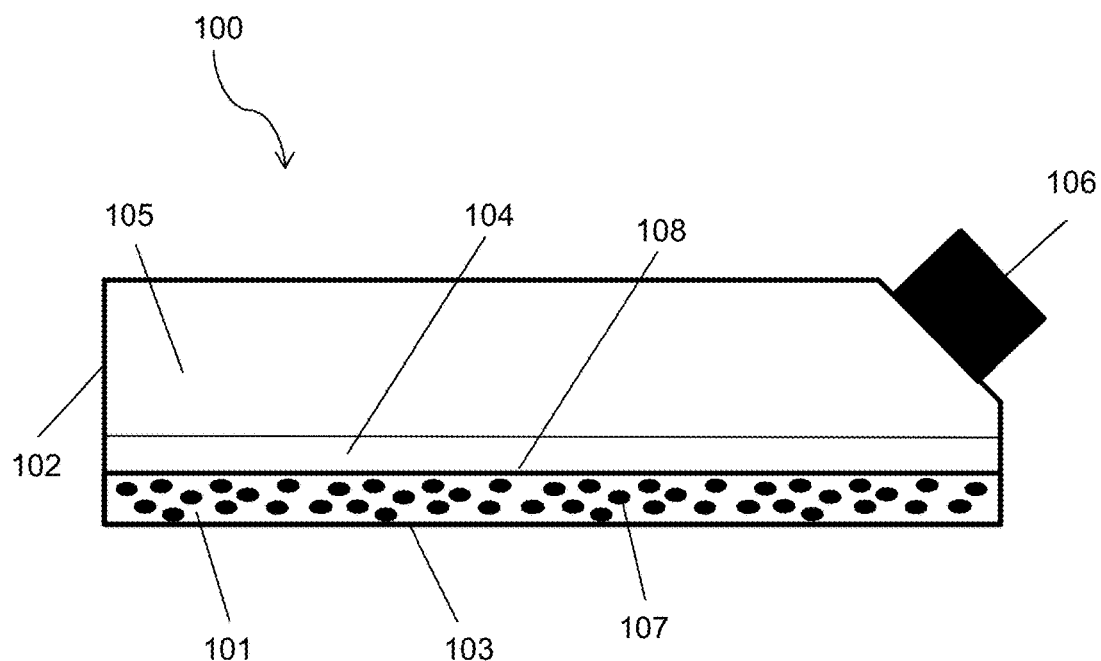
FIG. 13 is a schematic cross-sectional diagram of one embodiment of a three-dimensional cell culture system contemplated by the present invention

The present disclosure is generally directed to a three-dimensional cell culture system that includes a keratin-based hydrogel precursor solution. The system can allow for the cultivation and expansion of primary cells harvested from mammalian tissue and can mimic the process of two-dimensional cell culture systems on plates, flasks, or dishes but in a three-dimensional configuration to support normal cell growth and phenotype. Referring to FIG. 13, the system 100 includes a cell culture vessel 102 having a surface 103 (e.g., polystyrene, glass, etc.) on which the keratin-based hydrogel 101 is disposed. The keratin-based hydrogel 101 can be formed from a keratin-based polymer precursor solution and can contain a suspension of cells 107 which are encapsulated by the hydrogel 101. The system can also include a cap 106. The cap 106 can be vented to allow for gas flow, and cell culture medium 104 can be introduced to the system 100 when the cap 106 is removed. The space above the cell culture medium 104 can include air enriched with carbon dioxide 105 to promote the desired cell culturing conditions. It is also to be understood that rather than encapsulating the cells 107 within the keratin-based hydrogel 101, the cells 107 can be disposed on a surface 108 of the keratin-based hydrogel 101 after it is formed. It is also to be understood that keratin-based hydrogel precursor solution can also be used in a three-dimensional culture system for growing three-dimensional tumor spheroids from cancer cells.

Figure 14:
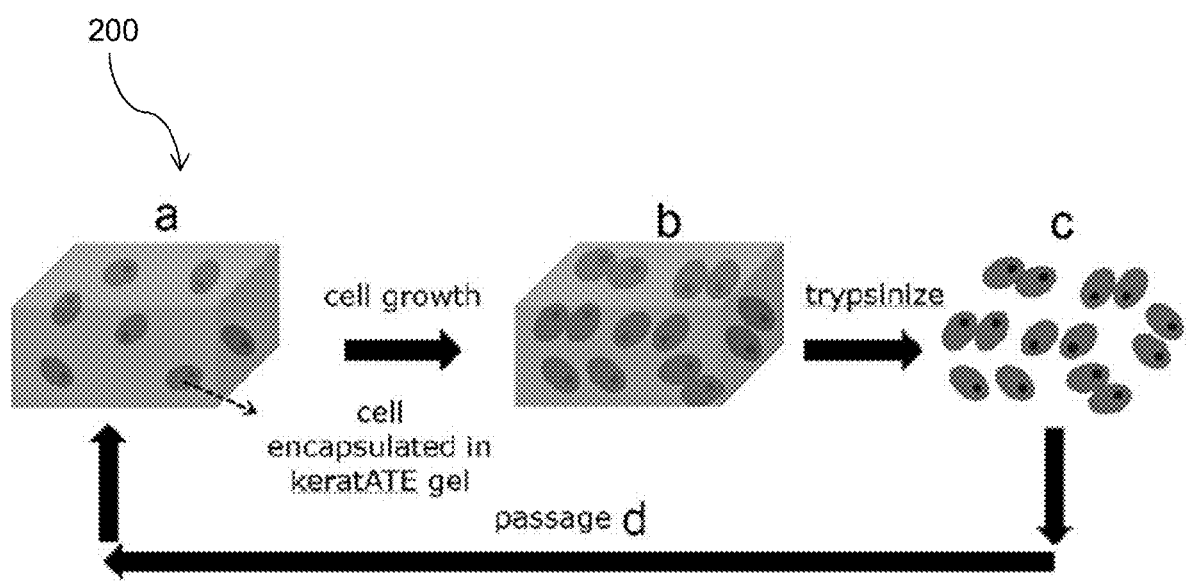
FIG. 14 is a schematic diagram showing a method of using the KeratATE hydrogel as a three-dimensional matrix for culturing, expanding, releasing, and passaging cells from isolated mammalian tissue as part of a three-dimensional cell culture system.

A method for culturing cells using the three-dimensional culture system 100 of FIG. 13 is also contemplated. For example, after a keratin-based hydrogel precursor solution is formed, mammalian cells can be added to the keratin-based hydrogel precursor solution and disposed on a surface of a cell culture vessel. The method 200 can include steps a, b, c, and d, as shown in FIG. 14. In step a, for example, cells harvested from mammalian tissue are added to a first keratin-based hydrogel precursor solution, where the cells are encapsulated in the hydrogel once it is formed on a cell culture surface. Specifically, the keratin-based hydrogel precursor solution/cell suspension is cast into a thin film on a surface of a cell culture vessel, and the thin film is then crosslinked with ultraviolet light. However, it is also to be understood that, alternatively, the cells can be added to a surface of the hydrogel once it is formed on a surface of the cell culture vessel and crosslinked. In any event, whether the cells are encapsulated within the hydrogel or seeded onto a surface of the hydrogel, the cells are allowed to grow within the resulting keratin hydrogel until they reach the desired confluency in step b, at which time trypsin is added to the cell culture system to detach the cells from the keratin hydrogel in step c. This is possible because the keratin hydrogel is susceptible to degradation by trypsin but not collagenase. The trypsinized cells are centrifuged to remove the trypsin, then, in step d, the cells are re-suspended in a fresh second keratin-based hydrogel precursor solution and plated into the desired number of cell culture vessels, at which time the method is repeated to continuously passage the primary cells.

One embodiment of a process for forming the keratin-based hydrogel precursor solution and a cross-linked keratin-based hydrogel formed from the precursor solution are shown in FIG. 1 and are discussed in more detail below. Generally, the method involves a) reducing or cleaving the disulfide bonds between the cysteine residues in keratin (e.g., keratin feather) to sulfhydryl groups followed by b) converting the free thiol groups to dehydroalanine by oxidative elimination, and followed by conversion of dehydroalanine to s-allyl cysteine to produce keratin allyl thioether (KeratATE). Next, the KeratATE is dissolved in an aqueous solution, a photo-initiator is added to the aqueous mixture, and the mixture is crosslinked into a KeratATE hydrogel using ultraviolet radiation.

More specifically, to form a keratin-based hydrogel precursor solution, keratin can initially be extracted from a natural source. This can be carried out according to known methodology, for instance by breaking disulfide bonds between the individual chains and without hydrolysis of the amide bonds so as to solubilize the keratin. In one embodiment, keratin extraction can be carried out by use of a combination of tris(2-carboxyethyl) phosphine (TCEP), sodium dodecyl sulfate (SDS), and urea. Urea acts as a first solubilizing agent to disrupt intra- and inter-molecular hydrogen bonds in the keratin, TCEP acts as a second solubilizing agent by reducing disulfide bridges to form sulfhydryl groups, and SDS serves a surfactant for stabilization of the solubilized keratin molecules within the aqueous solution.

Of course, the extraction process is not limited to this particular methodology, and any extraction process can be utilized that can reduce disulfide bridges of the natural material without hydrolysis of the protein, so as to produce a relatively monodisperse solubilized protein composition. Following the disulfide bridge reduction, the solubilized keratin polymer can include few or no remaining disulfide bridges. For instance, about 10% or less of the cysteines of the solubilized polymer can be bonded via disulfide bonds. In general, the solubilized protein can include from about 75 to about 7500 amino acids and can have a molecular weight of from about 7.5 kDa to about 75 kDa.

Following extraction, the solubilized keratin polymer can be functionalized to include reactive functionality suitable for crosslinking the polymer to form a hydrogel network. More specifically, the reactive functionality can be bonded to the keratin via reaction of the sulfhydryl groups of the cysteines and can be such that crosslinking is controllable (i.e., the reactive functionality will not react at the conditions expected to be encountered during formation, storage, and delivery of the aqueous composition). As such, the composition can be delivered to a two-dimensional cell culture surface of interest and can then be crosslinked.

The reactive functionality can be configured for crosslinking according to any desirable reaction scheme. In one preferred embodiment, the keratin-based polymer can be modified with a reactive functionality configured for crosslinking via photopolymerization by use of ultraviolet (UV) radiation, infrared (IR) radiation, visible light, or any combination thereof. Examples of photopolymerizable functionality can include, without limitation, allyls, acrylates, diacrylates, oligoacrylates, methacrylates, dimethacrylates, oligomethacrylates, etc., or any combination thereof.

A keratin-based polymer is not limited to photopolymerization, however, and reactive functionality configured for chemical crosslinking, thermal crosslinking, or any other controllable crosslinking reaction scheme or combination thereof can be utilized in conjunction with or alternative to photopolymerizable functionality. By way of example and without limitation, the polymer can include as reactive functionality carboxylic acids, anhydrides, esters, unsaturated epoxies, etc.

In one embodiment, functionalization of the solubilized keratin can be carried out such that the secondary structure of the keratin is affected to little or no degree. This may be beneficial in providing a crosslinked hydrogel exhibiting a stable, honeycomb-shaped pore structure (see FIG. 2) without the necessity of blending with other polymers such as chitosan, silk fibroin, or collagen (though, in some embodiments, it may be desirable to form the hydrogel from a combination of natural polymers).

Functionalization of the solubilized keratin polymer can be carried out according to any suitable chemistry. For example, in one embodiment, the sulfhydryl groups of the polymer can be reacted directly with a bi-functional monomer that includes the reactive functionality to form the functionalized polymer in a single-step process. In another embodiment, a multi-step process can be carried out. For instance, in one embodiment described further in the examples section below, a two-step reaction process can be carried out to functionalize sulfhydryl groups of solubilized keratin. In the first step, sulfhydryl groups of cysteines on the keratin can be converted to an intermediate group, for instance by oxidative elimination. In a second step, the intermediate groups can then be converted to include the desired reactive functionality (e.g., an allyl group) and produce the keratin-based polymer, which may be crosslinked to form a hydrogel network.

The aqueous composition that includes the functionalized keratin-based polymer can include additional components as desired. For instance, in one embodiment, the polymer can be crosslinked by use of an initiator that is activated by UV radiation (UV initiators), visible light (light initiators), heat (thermal initiators), or chemical initiators. The composition can include the initiator in conjunction with the polymer or an initiator can be combined with the composition at the time of crosslinking. For instance, an initiator can be provided in a separate composition and combined with the aqueous composition that includes the keratin-based polymer at the time of injection of the composition to the site of interest and shortly prior to crosslinking.

Examples of initiators can include, without limitation, acetophenone, 2,2-dimethoxy-2-phenol-acetophenone ("DMPA") (UV initiators), camproquinone, ethyl-4-N,N,-dimethyl aminobenzoate (light initiators), benzoyl peroxide (thermal initiator), or ammonium persulfite (chemical initiator). In one particular embodiment, the photoinitiator can be 4-(2-hydroxyethoxy)phenyl-(2-hydroxy-2-propyl)ketone (Irgacure 2959). Preferred initiators can depend not only upon the particular reactive functionality of the polymer, but also upon the expected application of the hydrogel. For instance, when considered for use for in vivo applications, a suitable initiator for internal use should be utilized.

In some embodiments, the composition can include a crosslinking agent configured for reaction with the reactive functionality of the polymer. A crosslinking agent can be a polyfunctional compound or combination thereof that can react with the reactive functionality of the polymer to form crosslinks within and among the keratin polymers in formation of the hydrogel. In general, a crosslinking agent can be a non-polymeric compound, i.e., a molecular compound that includes two or more reactively functional terminal moieties linked by a bond or a non-polymeric (non-repeating) linking component. By way of example, a crosslinking agent can include but is not limited to di-epoxides, poly-functional epoxides, diisocyanates, polyisocyanates, polyhydric alcohols, water-soluble carbodiimides, diamines, diaminoalkanes, polyfunctional carboxylic acids, diacid halides, and so forth.

In one particular embodiment, forming a hydrogel from keratin can include a) reducing the disulfide bonds between the cysteine residues in keratin to sulfhydryl groups followed by b) converting the free thiol groups to dehydroalanine by oxidative elimination, and followed by conversion of dehydroalanine to s-allyl cysteine to produce keratin allyl thioether (KeratATE). Next, the KeratATE is dissolved in aqueous solution, a photo-initiator is added to the aqueous mixture, and the mixture is crosslinked into a hydrogel by ultraviolet radiation.

Figure 2:
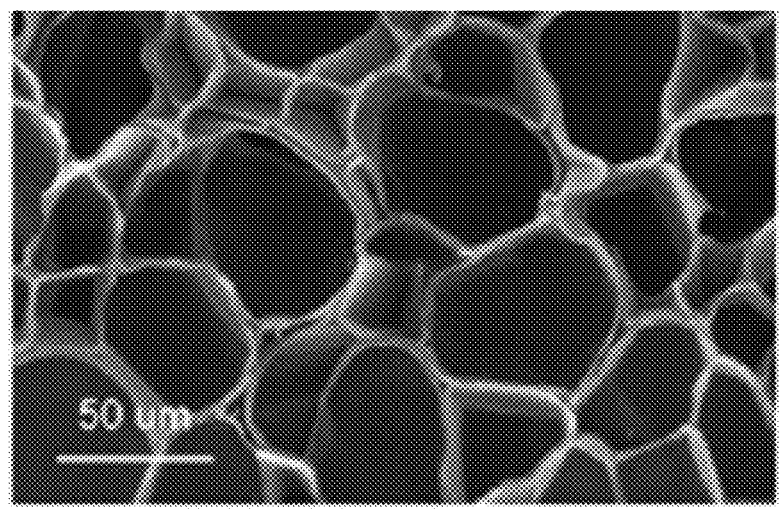
FIG. 2 represents a scanning electron microscopy (SEM) image of a 15 wt. % keratin allyl thioether (KeratATE) solution after ultraviolet (UV) crosslinking.

The keratin-based hydrogel precursor solution, to which any desired cell suspension has been added, can be disposed on a surface of a cell culture vessel and crosslinked via reaction of the reactive functionality to form a hydrogel that has a honeycomb microstructure with microchannels in the 2 micrometer to 200 micrometer size range, as shown in FIG. 2. Cells to be cultured in the three-dimensional cell culture system of the present invention can be encapsulated within the honeycomb microstructure in a three-dimensional arrangement to facilitate their proper growth and maintenance of the desired phenotype. The size distribution of the microchannels can be varied from about 2 micrometers to about 200 micrometers, for example, by varying the keratin-based polymer (e.g., KeratATE) concentration in the hydrogel precursor solution.

A hydrogel formed by crosslinking the reactive functionality of the keratin-based polymer can have a porous, interconnected, honeycomb microstructure. As the natural disulfide bridges of the keratin source are broken and functionalized with a controllable crosslinking moiety in formation of the hydrogel, the product hydrogel can have relatively few disulfide bonds as compared to previously known keratin-based hydrogels. For instance, the keratin-based hydrogels can include about 10% or less of the crosslinks of the hydrogel as disulfide bridges, or even less in some embodiments, for instance about 5% or less, or about 2% or less.

The pore size of the hydrogel can vary, but can generally be about 200 μm or less, for instance from about 10 μm to about 70 μm in some embodiments. Beneficially, the average pore size can be controlled by varying loading level of the keratin-based polymer in the hydrogel precursor solution.

Degradation rates of the hydrogels can be controlled in one embodiment through inclusion in the hydrogel of other polymers in conjunction with the keratin-based polymer. For instance, trypsin is known to cleave amino acid sequences containing arginine or lysine with long positively-charged side chains. Keratin contains about 4% arginine and no lysine whereas gelatin contains 9% arginine and 4.5% lysine amino acids. Further, gelatin contains —R-Pro-X-Gly-Pro-R— sequence where X is a neutral amino acid that is cleaved by collagenase whereas keratin has no such amino acids and is not targeted by collagenase. As a result, collagenase and trypsin can quickly degrade a hydrogel that includes a collagen-based polymer. Conversely, a keratin-based polymer can degrade relatively slowly in the presence of trypsin and is not susceptible to degradation by collagenase. Accordingly, through blending the disclosed keratin-based polymers with a collagen-based polymer and forming a composite hydrogel network, the degradation rate of the product hydrogel for use in an environment with known trypsin and collagenase concentrations can be controlled based upon the relative amounts of the biopolymers contained in the composite matrix. Thus, hydrogels can be formed having tunable degradation rates for use in particular applications and environments through co-polymerization of blends of the functionalized keratin-based polymers with other biopolymers such as collagen based polymers.

The hydrogel networks are well adapted for encapsulating cells. For example, in one embodiment from about $10^5$ to $10^8$ cells/cm$^3$ can be encapsulated within a hydrogel network. Beneficially, as the precursor solution is crosslinkable in situ, in one embodiment, the aqueous keratin-based hydrogel precursor solution can be combined with the cells in a suspension. The suspension can then be disposed on a surface of a cell culture vessel followed by crosslinking so as to form the hydrogel network directly on the cell culture surface, where the cells are encapsulated within the hydrogel.

In one particular embodiment, the cells can be mammalian cells, for instance human cells. The cell type is not limited. For example, the cells can include, without limitation, connective tissue cells, organ cells, muscle cells, nerve cells, and any combination thereof. In more specific embodiments, the cells can include tenocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, chondrocytes, or bone-forming cells. In some embodiments in which encapsulated cells are non-proliferating cells, the non-proliferating cells can include pancreatic islets, hepatic cells, neural cells, renal cortex cells, vascular endothelial cells, thyroid and parathyroid cells, adrenal cells, thymic cells, ovarian cells, or chondrocytes. In some embodiments, the cells can be stem cells, including but not limited to, mesenchymal stem cells, bone marrow-derived stem cells, embryonic stem cells, umbilical cord-derived stem cells, placenta-derived stem cells, or amniotic fluid-derived stem cells. In other embodiments, the cells can be cancer cells.

Figure 3:
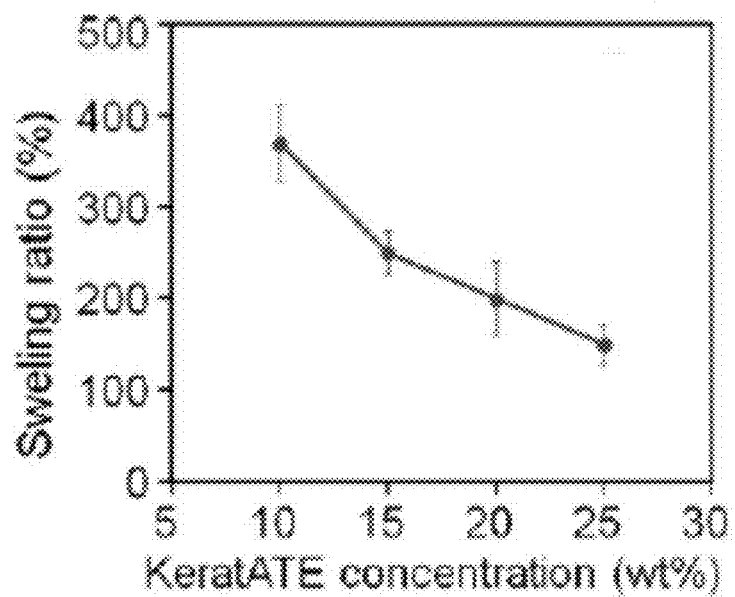
FIG. 3 illustrates the effect of KeratATE concentration on the swelling ratio of a crosslinked hydrogel. It is noted that the error bars correspond to the mean±1 standard deviation for a sample size of n=3.
Figure 4:
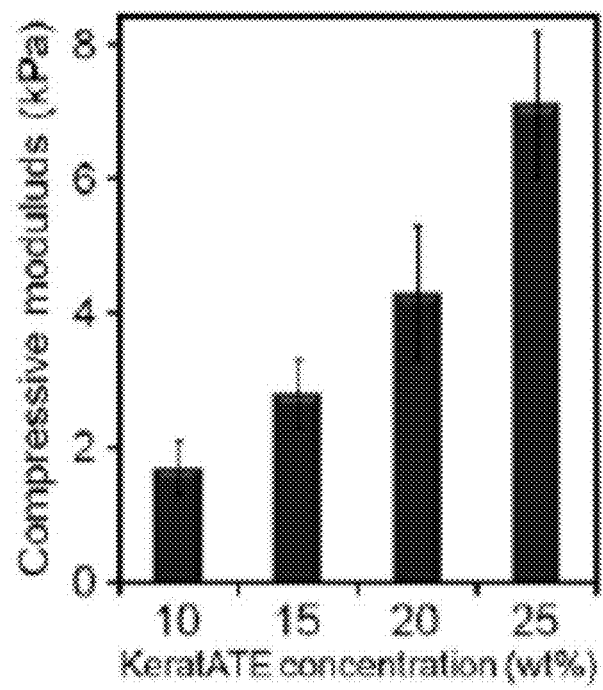
FIG. 4 illustrates the effect of KeratATE concentration on the compressive modulus of the crosslinked hydrogel. It is noted that the error bars correspond to the mean±1 standard deviation for a sample size of n=3.

The KeratATE hydrogels in the three-dimensional cell culture system of the present invention have a water content of greater than 50% (greater than 100% percent swelling) after crosslinking, as shown in FIG. 3, which implies that soluble proteins and growth factors can readily diffuse in the matrix to interact with encapsulated cells. Further, unlike the substrate in two-dimensional cell culture vessels, the stiffness or modulus of keratin hydrogels can be tuned to the desired value by changing the keratin-based polymer (e.g., KeratATE) concentration in the precursor solution, as shown in FIG. 4. For example, in some embodiments, the compressive modulus of the hydrogel can be about 10 kilopascals (kPa) or less, such as from about 1 kPa to about 8 kPa in some embodiments, with the modulus being controllable by polymer concentration in the precursor solution.

Figure 5:
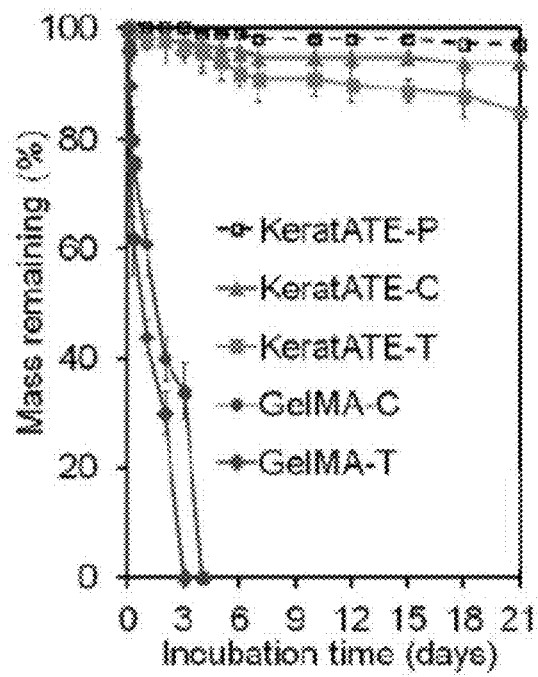
FIG. 5 illustrates the effect of incubation time on the mass loss of 15 wt. % KeratATE and 10 wt. % gelatin methacryloyl (GelMA) hydrogels incubated in PBS (P), PBS supplemented with trypsin (T, 2500 USP U/mL) or collagenase (C, 2.5 U/mL). It is noted that the error bars correspond to the mean±1 standard deviation for a sample size of n=3.
Figure 6:
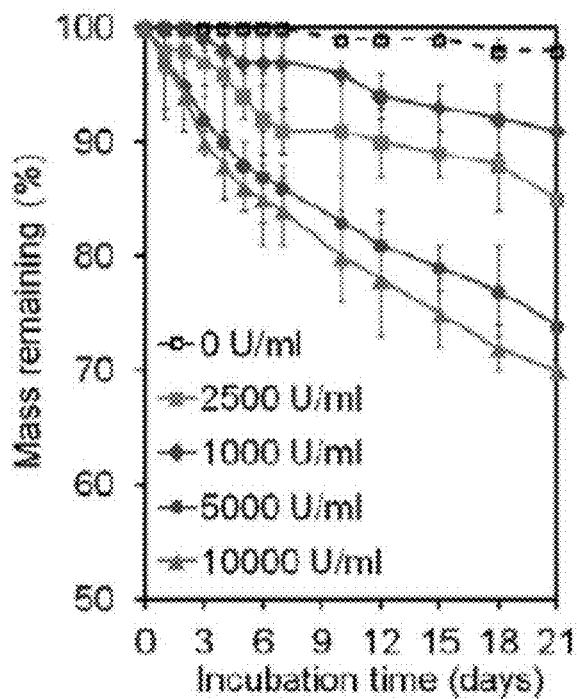
FIG. 6 illustrates the effect of trypsin concentration in PBS on mass loss of KeratATE hydrogel with incubation time. It is noted that the error bars correspond to the mean±1 standard deviation for a sample size of n=3.

In addition, unlike collagen hydrogels, the KeratATE hydrogels contemplated for use in the three-dimensional cell culture system of the present invention are not susceptible to degradation by MMPs, which are enzymes secreted by tissue cells, as shown in FIG. 5. For instance, the KeratATE hydrogels used in the three-dimensional cell culture system of the present invention retained at least about 80%, such as from about 80% to about 100%, such as from about 90% to about 99%, such as from about 94% to about 98% of their mass for up to 21 days when exposed to PBS supplemented with 2.5 U/milliliter of MMPs (collagenase C). Further, the KeratATE hydrogels also retained at least about 80%, such as from about 80% to about 100%, such as from about 81% to about 99%, such as from about 82% to about 98% of their mass for up to 21 days when exposed to PBS supplemented with 2500 USP U/milliliter of trypsin. On the other hand, the GelMA collagen hydrogels degraded readily in a few days in phosphate buffer saline (PBS) supplemented with 2.5 U/mL of MMPs (collagenase C) or 2500 USP U/mL of trypsin T. However, it should be noted that KeratATE hydrogel is susceptible to degradation by trypsin with the extent of degradation dependent on trypsin concentration, as shown in FIG. 6, where the trypsin concentration in PBS can be increased to up to 10,000 U/milliliter to facilitate detachment of encapsulated cells from the KeratATE hydrogel when the cells have reached the desired confluency within the hydrogel and require passaging. Conversely, KeratATE hydrogel is not susceptible to degradation by MMPs (collagenase) even as the MMP concentration increased, as shown in Figure FIG. 7. This indicates that the KeratATE hydrogel precursor solution and resulting hydrogel can be used in the three-dimensional cell culture system of the present invention since minimal degradation in the presence of collagenase occurs, which allows for the use of the hydrogel as a suitable cell culture substrate since it does not degrade when cells express collagenase, yet trypsin can be used to detach cells from the KeratATE hydrogel when passaging of the cells is required.

Figure 11:
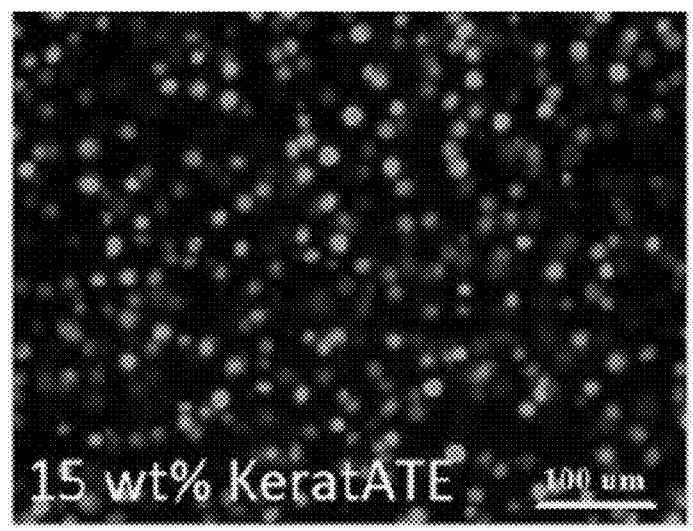
FIG. 11 illustrates a stained image of live MSCs encapsulated in a 15 wt. % KeratATE hydrogel after 8 hours of incubation time.
Figure 12:
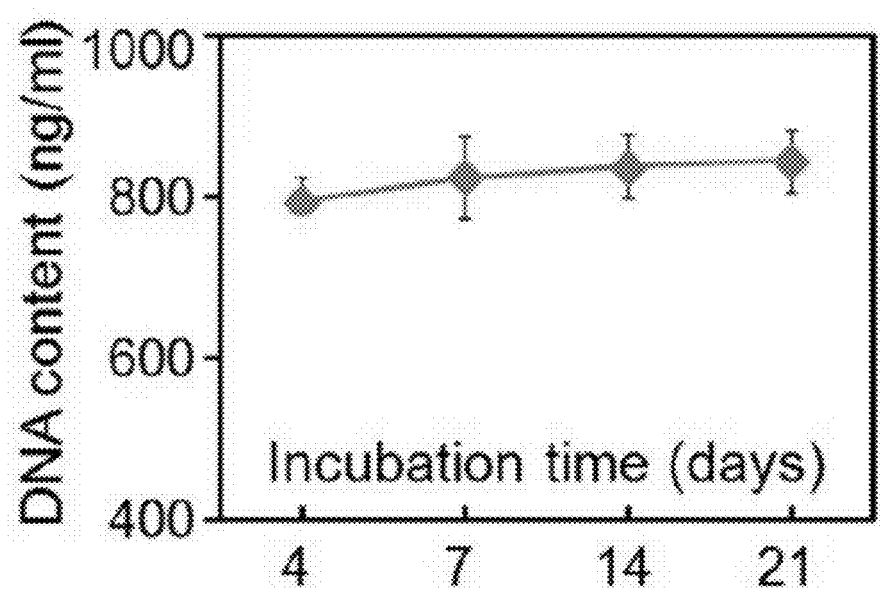
FIG. 12 illustrates the DNA content of MSCs encapsulated in a 15 wt. % KeratATE hydrogel from after 4 to 21 days of incubation time.

Further, mesenchymal stem cells (MSCs) seeded on KeratATE hydrogel spread and formed elongated spindle-shape morphology (FIG. 9), similar to the morphology of MSCs on a collagen-derived hydrogel (FIG. 8), as shown in the stained images. Further, cell density of MSCs seeded on a KeratATE hydrogel contemplated by the three-dimensional cell culture system of the present invention can increase with the same rate as those MSCs seeded on a collagen-derived hydrogel. Furthermore, when mesenchymal stem cells (MSCs) were encapsulated in a KeratATE hydrogel and cultured in basal medium without growth factors, at least about 95% of the encapsulated cells were viable 8 hours after encapsulation, as shown in FIG. 11. In addition, the cell content increased with incubation over a time period of 21 days, as shown in FIG. 12, where the increase in DNA content in nanograms/milliliter is indicative of an increase in cell number. For instance, the DNA content of cells cultured using the three-dimensional cell culture system of the present invention can range from about 600 nanograms per milliliter to about 1000 nanograms per milliliter, such as from about 650 nanograms per milliliter to about 950 nanograms per milliliter, such as from about 700 nanograms per milliliter to about 900 nanograms per milliliter after up to about 21 days in culture.

The present disclosure may be better understood with reference to the Example set forth below.

EXAMPLE

Materials

Chicken feather was obtained from Feathered Egg Company (Portland, Oreg.). Diethyl ether, allyl mercaptan, sodium dodecyl sulfate (SDS) and tris(2-Carboxyethyl) phosphine (TCEP) were purchased from VWR (Bristol, Conn.). 0-(2,4,6-Trimethylbenzenesulfonyl)hydroxylamine (MSH) was purchased from Angene International Limited (London, England). 5,5'-Dithiobis-(2-Nitrobenzoic Acid) (DTNB) reagent was purchased from Sigma-Aldrich (St. Louis, Mo.). All Fmoc-protected amino acids, the Rink Amide NovaGel™ resin and hydroxybenzotriazole (HOBt) were purchased from EMD Biosciences (San Diego, Calif.). 1,1,1,3,3,3-hexafluoro-2-propanol (HFIP), N,N-dimethylformarnide (DMF), dichloromethane (DCM), 4-dimethylaminopyridine (DMAP), diisopropylcarbodiimide (DIC), triisopropylsilane (TIPS), and trifluoroacetic acid (TFA) were received from Acros (Fairfield, Ohio). Phosphate-buffer saline (PBS) and Dulbecco's Modified Eagle's Medium (DMEM) were purchased from GIBCO BRL (Grand Island, N.Y.). Trypsin and fetal bovine serum (FBS) were received from Invitrogen (Carlsbad, Calif.) and Atlas Biologicals (Fort Collins, Colo.), respectively. Collagenase type 3 was purchased from Worthington (Lakewood, N.J.). Vinculin Monoclonal Antibody, Goat Anti-Mouse IgG Antibody-(H+L) FITC Conjugated, Goat Anti-Mouse IgG Antibody-(H+L) Texas-red Conjugated, TRITC-conjugated Phalloidin and 4,6-diarnidino-2-phenylindole (DAPI) were purchased from EMD Millipore (Billerica, Mass.).

Procedures

Feathers were cleaned by soaking in ether followed by washing with soapy water. The cleaned feathers were dried and cut into small pieces. 1 gram of feather was immersed in 100 mL of deionized water (DI) containing 0.5 M SDS, 8 M urea, and 50 mM TCEP. Next, the mixture was heated to 50° C., pH was adjusted to 6.5 and the aqueous solution was continuously stirred for 6 h to cleave disulfide bonds (FIG. 1, first step). Following, the solution was filtered (5 μm pore-size filter paper) and centrifuged at 10,000 rpm to remove undissolved feather. The filtered solution was dialyzed against DI water with a 3.5 kDa molecular weight (MW) cutoff dialysis tube for 3 days at ambient condition with changes in DI water every 6 hours. Finally, the keratin solution was frozen and freeze-dried.

A two-step reaction was used to functionalize the treated keratin at cysteine residues. The first reaction was oxidative elimination of sulfhydryl groups of cysteine to dehydroalanine (Dha) using MSH (FIG. 1, second step). Briefly, keratin was dissolved in a 50 mM sodium phosphate buffer supplemented with 1 mM TCEP. Next, the solution was placed in an ice bath and MSH was added to the solution dropwise. The reaction ran for 20 minutes under stirring. The conversion of cysteine to Dha using MSH is reported to be rapid and reach complete conversion. After heating the mixture to ambient condition, allyl mercaptanol was added to the reaction with the same molar ratio as MSH to convert Dha to S— allyl cysteine (allylation) and form keratin allyl thioether (FIG. 1, third step). The reaction ran for 24 hours under stirring. The reaction product was collected in several time intervals between 30 minutes and 24 hours to investigate the effect of reaction time on conversion of Dha. Finally, the product was dialyzed against DI water for 4 days with a change of medium every 6 hours and lyophilized. The product, keratin allyl thioether, is hereafter denoted herein by KeratATE.

SDS-PAGE analysis was used to determine the molecular weight of keratin. Extracted keratin solutions (before and after functionalization) were diluted 1:1 with 2× sample buffer (BioRad, Hercules, Calif.) with 5% 2-mercaptoethanol. The proteins (0.2 mL samples) were separated using a vertical slab gel electrophoretic system with a 4-15% stacking gel. Electrophoresis was performed at 100 V and 15 mA for 90 min. The proteins in the gel were stained with 0.5 g/L Coomassie brilliant blue R-250, 10% acetic acid, and 50% methanol for 1 h and de-stained in 10% acetic acid and 45% ethanol.

The molecular weight of keratin was determined qualitatively by dialysis method using dialysis tubes with MW cutoffs of 6-8 kDa and 12-14 kDa. The extracted keratin at a concentration of 10 mg/mL was dissolved in sodium phosphate buffer with 1 mM TCEP. Then, the keratin solution was transferred to the dialysis tube and dialyzed against DI water for 4 days with change of DI water every 6 h. At the end of dialysis, the keratin solution was collected from the tubes, freeze-dried and the protein weight was measured. The percent by weight of protein remaining in the dialysis tube (P) was calculated using the following equation:

$$P = \frac{wi - wf}{wi} \times 100$$

where wi and wf are the initial and final weights of the protein in the dialysis tube.

The functionalized keratin was dissolved in aqueous solution and crosslinked by ultraviolet-initiated polymerization. Briefly, the photo-initiator (Irgacure 2959; CIBA, Tarrytown, N.Y.) was dissolved in PBS at 50° C. by vortexing. The hydrogel precursor solution was prepared by mixing the solution of macromer in PBS (10 mg/mL) with the photo-initiator solution and vortexing. The macromer was KeratATE or GelMA. The hydrogel precursor solution was degassed and transferred to a polytetrafluoroethylene (PTFE) mold (5 cm×3 cm×750 mm), the mold was covered with a transparent glass plate and fastened with clips. Next, the samples were irradiated with a BLAKRAY 100 W mercury, long wavelength (365 nm) UV lamp (B100-AP, UVP, Upland, Calif.) for 5 min to complete the crosslinking reaction. It should be noted that the UV lamp was used to follow the kinetics of gelation of KeratATE precursor solution whereas the high-intensity Omni Cure UV illumination system was used for cell encapsulation in KeratATE hydrogel (see below). Disk-shaped samples were cut from the gel using an 8-mm cork borer and loaded on the Peltier plate of the TA rheometer and subjected to a uniaxial compressive force at a displacement rate of 7.5 mm/s. The slope of the linear fit to the stress-strain curve for 5%-10% strain was taken as the compressive modulus of the gels.

To measure the swelling ratio of keratin hydrogels, disk shape samples with diameter of 8 mm and thickness of 750 mm were dried at ambient conditions for 12 h followed by drying in vacuum for 1 h at 40° C. After drying, the dry weights (wi) were recorded. Next, the dry samples were swollen in DI water for 24 h at 37° C. with a change of swelling medium every 6 h. After swelling, the surface water was removed and the swollen weights (ws) were measured. Then, the swollen samples were dried as described above and the dry weights (wd) were recorded. The swelling ratio (Q) was calculated from the dry and swollen weights The microstructure of keratin hydrogel was imaged using a VEGA3 SBU variable pressure scanning electron microscope (SEM; Tescan, Kohoutovice, Czech Republic) at 8 KeV accelerating voltage. The lyophilized samples were broken to expose a freshly cut surface for imaging, coated with gold a using a Denton Desk II sputter coater (Moorestown, N.J.) at 20 mA for 75 sec, and imaged with SEM.

Disk shaped samples with diameter of 8 mm and thickness of 750 mm were dried at ambient conditions for 12 h followed by drying in vacuum for 1 h at 40° C. to measure the initial dry weight. Then, the hydrogels were incubated in 5 mL of either PBS, different concentrations of trypsin dissolved in PBS (0, 1000, 2500, 5000, 10000 USP U/mL) or collagenase type 3 dissolved in PBS (0, 1, 2.5, 5, and 10 U/ml) at 37° C. under mild agitation. At each time point, samples were washed with DI water to remove excess electrolytes, dried under vacuum, and the dry sample weights were measured and compared with the initial dry weights to determine fractional mass remaining.

hMSCs (Lonza, Allendale, N.J.) were cultivated at 5000 cells/cm$^2$ in a high glucose DMEM medium supplemented with 10% FBS, 100 units/mL penicillin and 100 100 μg/mL streptomycin (basal medium). After reaching 70% confluency, the cells were detached with 0.1% trypsin-0.03% EDTA and sub-cultivated at a ratio of 1:3 for <5 passages, according to supplier's instructions. 24-well tissue culture plates were coated with a thin layer of the hydrogel precursor solution (KeratATE or GelMA) with a concentration of 15 wt. % in PBS. The precursor solutions in the wells were crosslinked by UV as described above for two minutes. Next, hMSCs were seeded on the surface of the gels at a density of 5×10$^3$ cells/cm$^2$ and cultured in basal medium for cell attachment. At each time point (1, 2, 4, 6 and 7 days), cell-seeded hydrogels were washed with serum-free DMEM for 8 h followed by washing with PBS. Next, samples were lysed with 10 mM Tris supplemented with 0.2% triton in PBS and the lysed samples were used for measurement of DNA content using Quant-it PicoGreen. GelMA coated well plates were used as controls.

For cell viability, disks were stained with cAM/EthD live/dead assay to image live and dead cells, respectively. Stained samples were imaged with an inverted fluorescent microscope (Nikon Eclipse Ti-E, Nikon, Melville, N.Y.). For immunofluorescent staining, cell-seeded hydrogels were washed twice in PBS and fixed with 4% paraformaldehyde (Sigma-Aldrich) at 4° C. for 12 h. Next, samples were permeabilized with 0.1% Triton X-100 and 100 mM glycine in PBS for 1 h and blocked with 1.5% BSA and 0.5 mM glycine in PBS for 2 h. Then, samples were incubated with primary antibody (vinculin monoclonal antibody) in PBS containing 1% BSA for 24 h at 4° C. according to manufacturer's instructions. After washing with PBS, samples were incubated with goat anti-mouse conjugated FITC or goat anti-mouse conjugated Texas-red secondary antibody and TRITC-conjugated phalloidin in blocking buffer for 2 h at ambient conditions. The cell-seeded hydrogel samples were counter-stained with DAPI to image cell nuclei.

For cell encapsulation, 1×10$^6$ hMSCs, suspended in 100 1-1 L of PBS, were added to the KeratATE precursor solution and mixed gently with a pre-sterilized glass rod. The density of MSCs in the gel was 1×10$^6$ cells/mL. The mixture was injected between two sterile microscope glass slides and crosslinked by UV irradiation with an OmniCure Series S1500 UV Spot illumination system (200 W lamp) with 8-mm diameter light guide. The high-intensity Omni Cure system was used for cell encapsulation to sharply reduce the crosslinking time and exposure of the encapsulated cells to UV light. The gel precursor solutions were irradiated for 180 seconds which was the minimum time for the gels to reach their plateau modulus. After crosslinking, the gel samples were cut into disks and the disks were incubated in 2 mL of PBS for 1 hour with two medium changes. Next, the medium was replaced with basal medium and hMSCs encapsulated in the gels were incubated for 21 days. Experimental groups included hMSCs encapsulated in KeratATE hydrogel. At each time point (4, 7, 14, and 21 days), the samples were evaluated by biochemical, mRNA, and immunohistochemical analysis.

For immunofluorescent staining, the adhered cells on KeratATE disks were washed twice in PBS and fixed with 4% paraformaldehyde (Sigma-Aldrich) at 4° C. for 12 hours. Next, samples were permeabilized with 0.1% Triton X-100 and 100 mM glycine in PBS for 1 h and blocked with 1.5% BSA and 0.5 mM glycine in PBS for 2 hours. Then, samples were incubated with primary antibody (vinculin monoclonal antibody) in PBS containing 1% BSA for 24 hours at 4° C. according to manufacturer's instructions. After washing with PBS, samples were incubated with goat anti-mouse conjugated FITC or goat anti-mouse conjugated Texas-red secondary antibody and TRITC-conjugated phalloidin in blocking buffer for 2 hours at ambient conditions. Each sample was counterstained with DAPI to image the cell nuclei. Stained samples were imaged with an inverted fluorescent microscope (Nikon Eclipse Ti-ε, Nikon, Melville, N.Y.). For cell viability, the unfixed samples were stained with cAM/EthD live/dead assay (1 μg/mL) and imaged with the inverted fluorescent microscope to image live and dead cells, respectively.

At each time point, part of the MSC-encapsulated KeratATE hydrogel samples were homogenized and sonicated to rupture membranes of the encapsulated cells. Double-stranded DNA (dsDNA) content of the homogenized samples was analyzed using a PicoGreen assay with a plate reader (Synergy HT, Bio-Tek, Winooski, Vt.).

Results

FIGS. 3 and 4 show the effect of KeratATE concentration in precursor solution on compressive modulus and water swelling ratio of the hydrogels crosslinked with high-intensity Omni Cure UV system, respectively. Compressive modulus of the hydrogels increased from 1.8±0.3 to 7.7±0.4 kPa with increasing KeratATE concentration from 10 to 25 wt. % (FIG. 3), respectively, whereas swelling ratio in PBS decreased from 390±40% to 150±25% (FIG. 4).

Figure 7:
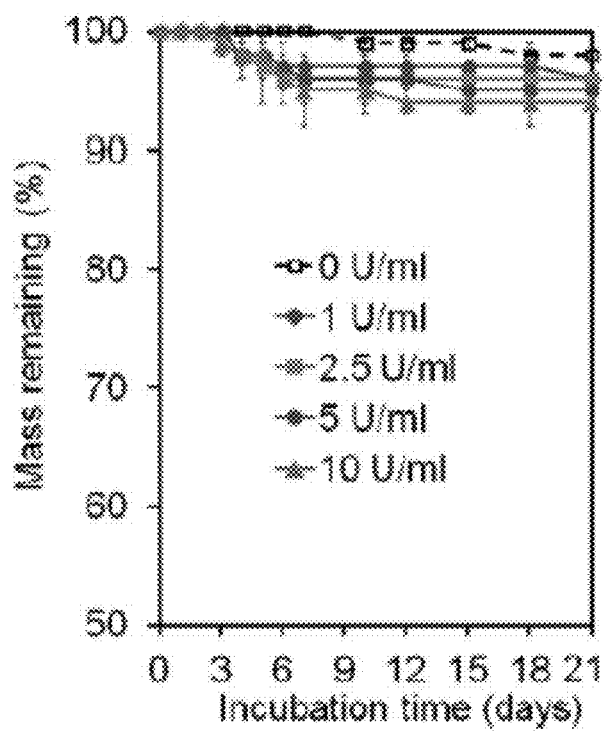
FIG. 7 illustrates the effect of collagenase concentration in PBS on the mass loss of KeratATE hydrogel with incubation time. It is noted that the error bars correspond to the mean±1 standard deviation for a sample size of n=3.

FIG. 5 compares the mass loss of a KeratATE hydrogel (20 wt. %) with GelMA (10 wt. %) in PBS (P), trypsin with 2500 USP U/mL concentration (T), and collagenase with 2.5 U/mL concentration. KeratATE and GelMA hydrogels showed no mass loss in PBS after 21 days. The GelMA collagen-based hydrogel completely degraded in collagenase and trypsin solutions in less than 5 days. Conversely, the KeratATE hydrogel showed less than 5% mass loss in collagenase solution and less than 15% mass loss in trypsin after 21 days incubation. Meanwhile, FIG. 6 shows that mass loss of a KeratATE hydrogel was strongly dependent on trypsin concentration. Mass loss of a KeratATE hydrogel increased from 9±3 to 15±4 to 26±2 to 30±3 wt. % after 21 days as trypsin concentration in incubation solution was increased from zero to 1000 to 2500 to 5000 to 10000 U/mL, respectively. On the other hand, FIG. 7 shows that mass loss of a KeratATE hydrogel was not significantly affected by an increase in collagenase concentration. These degradation results demonstrate that KeratATE hydrogels possess higher enzymatic stability compared to the GelMA hydrogels.

Figure 8:
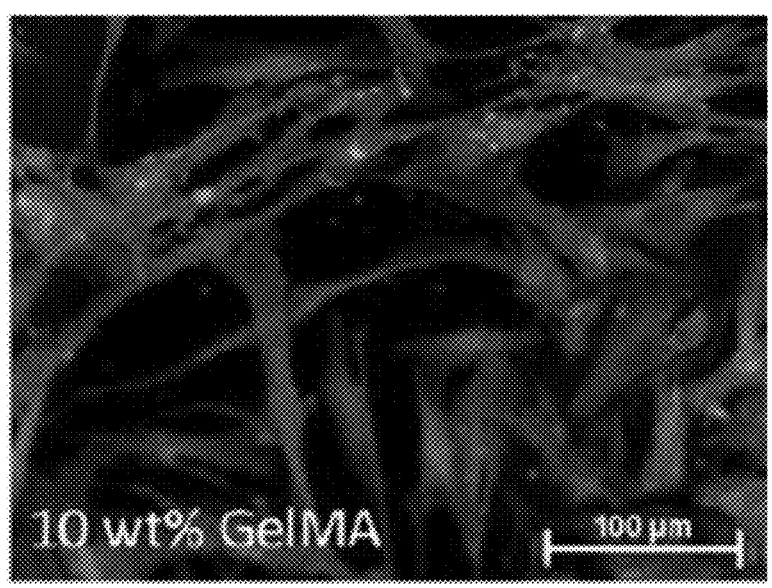
FIG. 8 is a DAPI (blue), phalloidin (red), and vinculin (green) stained image showing the spindle-like shape of mesenchymal stem cells (MSCs) seeded onto a collagen-derived hydrogel (e.g., a gelatin methacryloyl (GelMA) hydrogel) after 7 days of incubation in basal medium, where the dots are representative of focal adhesion points.
Figure 9:
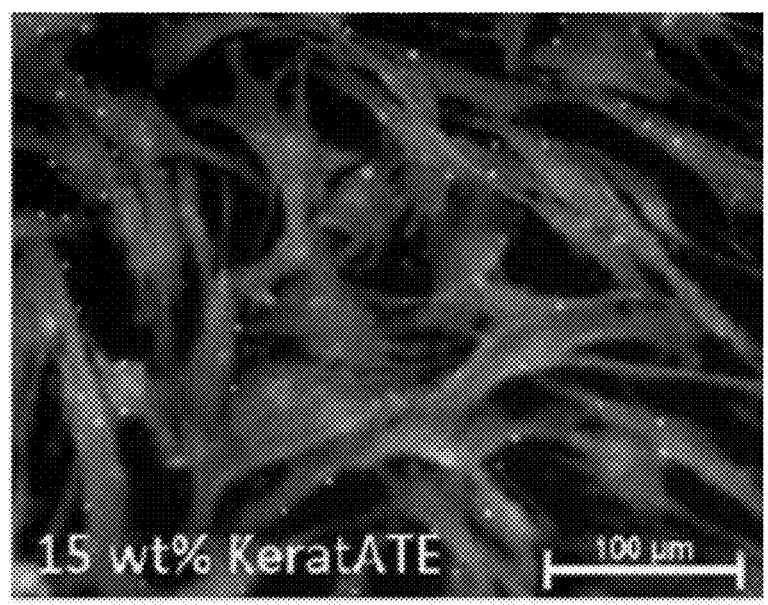
FIG. 9 is a DAPI (blue), phalloidin (red), and vinculin (green) stained image showing the spindle-like shape of mesenchymal stem cells (MSCs) seeded onto a KeratATE hydrogel after 7 days of incubation in basal medium, where the dots are representative of focal adhesion points.
Figure 10:
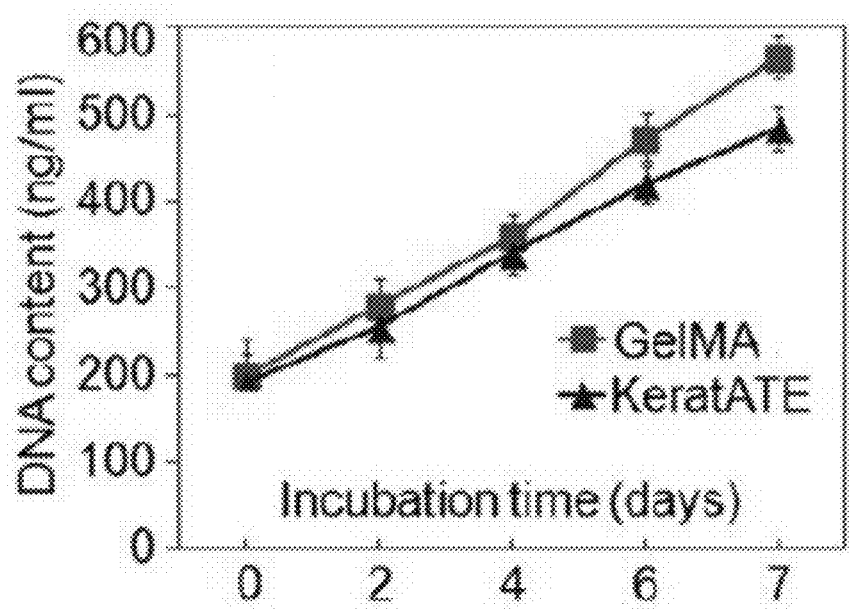
FIG. 10 illustrates the DNA content of MSCs seeded on collagen-derived (GelMA) and KeratATE hydrogels as a function of incubation time.

Immunostained images in FIGS. 8 and 9 show adhesion of hMSCs to GelMA and KeratATE surfaces, respectively. There was extensive cell adhesion to GelMA and the attached cells had elongated spindle-shape morphology. hMSCs seeded on KeratATE had an elongated morphology similar to those seeded on GelMA. Cell density on a KeratATE hydrogel surface was slightly lower than GelMA based on DNA content measurement (see FIG. 10). However, based on counting the number of stained cells, the density of hMSCs on the KeratATE surface increased was 29±0.5×10³ cells/cm² after 7 days, while the density of hMSCs on the GelMA surface was 27±0.6×10³ cells/cm² after 7 days. Further, the number of focal cell adhesion points (dots in the images) was high on the KeratATE surface (see FIG. 9).

FIG. 11 shows the live and dead hMSCs encapsulated in KeratATE hydrogels after encapsulation for 8 h. The fraction of viable hMSCs encapsulated in KeratATE hydrogels, quantified by dividing images into smaller squares and counting the number of live and dead cells was 92±2% after 8 hours.

DNA content for hMSCs encapsulated in KeratATE is shown in FIG. 12, with incubation time in basal medium, where the DNA content was at least 800 nanograms per milliliter over a time frame ranging from 4 to 21 days of incubation time.

While certain embodiments of the disclosed subject matter have been described using specific terms, such description is for illustrative purposes only, and it is to be understood that changes and variations may be made without departing from the spirit or scope of the subject matter.

What is claimed is:

1. A three-dimensional cell culture system comprising a cell culture vessel and a keratin-based hydrogel formed from a keratin-based hydrogel precursor solution, wherein the keratin-based hydrogel precursor solution comprises a solubilized keratin-based polymer comprising a reactive functionality bonded to the keratin-based polymer via cysteine residues of the polymer, wherein the keratin-based polymer comprises keratin allyl thioether, wherein about 10% or less of the cysteine residues of the solubilized keratin-based polymer are bonded via disulfide bridges.

2. The three-dimensional cell culture system of claim 1, wherein the keratin-based hydrogel precursor solution comprises a crosslink initiator, wherein the crosslink initiator comprises an ultraviolet crosslink initiator, a visible light initiator, a thermal initiator, or a chemical initiator.

3. The three-dimensional cell culture system of claim 1, wherein the keratin-based hydrogel is formed on a surface of the cell culture vessel.

4. The three-dimensional cell culture system of claim 3, wherein the surface comprises polystyrene or glass.

5. The three-dimensional cell culture system of claim 3, wherein the three-dimensional cell culture system is configured such that a suspension of cells is combined with the keratin-based polymer precursor solution before the keratin-based hydrogel is formed on the surface of the cell culture vessel, wherein the living cells are encapsulated within the keratin-based hydrogel.

6. The three-dimensional cell culture system of claim 3, wherein the three-dimensional cell culture system is configured such that a suspension of cells is disposed on a surface of the keratin-based hydrogel after the keratin-based hydrogel is formed on the surface of the cell culture vessel.

7. The three-dimensional cell culture system of claim 1, wherein the keratin-based hydrogel is susceptible to degradation by trypsin.

8. The three-dimensional cell culture system of claim 1, wherein the keratin-based hydrogel is not susceptible to degradation by collagenase.

9. A method of forming a three-dimensional cell culture system comprising a cell culture vessel and a keratin-based hydrogel, the method comprising:
    forming a keratin-based hydrogel precursor solution, the solution comprising a solubilized keratin-based polymer comprising a reactive functionality bonded to the keratin-based polymer via cysteine residues of the polymer, wherein the keratin-based polymer comprises keratin allyl thioether, wherein about 10% or less of the cysteine residues of the solubilized keratin-based polymer are bonded via disulfide bridges;
    delivering the keratin-based hydrogel precursor solution to a surface of the cell culture vessel; and
    following delivery, crosslinking the keratin-based polymer at the surface via reaction of the reactive functionality to form the keratin-based hydrogel.

10. The method of claim 9, wherein the keratin-based polymer is crosslinked via addition of energy to the keratin-based hydrogel precursor solution.

11. The method of claim 10, wherein the energy is in the form of ultraviolet radiation, visible light, or infrared radiation.

12. The method of claim 9, wherein the keratin-based polymer is crosslinked via addition of a crosslinking agent to the surface to form the keratin-based hydrogel.

13. The method of claim 12, wherein cells are added to the cell culture vessel after the crosslinking agent is added to the surface to form the keratin-based hydrogel, wherein the cells are delivered to a surface of the keratin-based hydrogel.

14. The method of claim 9, wherein cells are combined with the keratin-based hydrogel precursor solution before delivering the keratin-based hydrogel precursor solution to the surface of the cell culture vessel.

15. A method of culturing cells in a three-dimensional cell culture system comprising a cell culture vessel and a keratin-based hydrogel, the method comprising:
    combining a first keratin-based hydrogel precursor solution with the cells;
    delivering the first keratin-based hydrogel precursor solution containing the cells to a surface of the cell culture vessel to form a film;
    crosslinking the film to form the keratin-based hydrogel, wherein the keratin-based hydrogel includes a keratin-based polymer comprising a reactive functionality bonded to the keratin-based polymer via cysteine residues of the polymer, wherein the keratin-based polymer comprises keratin allyl thioether; and
    adding a layer of cell culture medium to the cell culture vessel.

16. The method of claim 15, further comprising introducing trypsin to the cell culture vessel to detach the cells from the keratin-based hydrogel.

17. The method of claim 16, further comprising separating the detached cells from the trypsin and combining a second keratin-based hydrogel precursor solution with the detached cells.

18. The method of claim 17, further comprising delivering the second keratin-based hydrogel precursor solution containing the detached cells to a surface of one or more new cell culture vessels.

* * * * *